United States Patent [19]

Mitchell

[11] Patent Number: Plant 7,158

[45] Date of Patent: Feb. 20, 1990

[54] VARIETY OF TROPICAL MANGO

[76] Inventor: Edward F. Mitchell, 13950 SW. 67 Ave., Miami, Fla. 33158

[21] Appl. No.: 155,478

[22] Filed: Feb. 12, 1988

[51] Int. Cl.[4] ..... A01H 5/00

[52] U.S. Cl. ..... Plt./33

[58] Field of Search ..... Plt./33

*Primary Examiner*—Robert E. Bagwill

*Attorney, Agent, or Firm*—Malin, Haley, McHale, DiMaggio & Crosby

[57] ABSTRACT

A new Mango tree which annually bears uniquely colored fruit on well spaced branches. The fruit has bright orange flesh and small seeds.

2 Drawing Sheets

BRIEF SUMMARY OF THE INVENTION

This invention relates to a new variety of mango that originated as a seedling of unknown origin. The new variety may contain Saigon genes. This variety, named Golden Nuggets, has been asexually reproduced by grafting. The growth habit is upright, vigorous with well spaced branching. It is an annual bearer and matures after the variety Tommy Atkins in August. The fruit is oval in shape, averages 16-17 ounces, has a bright golden skin when fully mature and has orange flesh and small seeds.

BRIEF DESCRIPTION OF THE DRAWINGS

FIG. 1 is a close-up photograph of my new mango.

FIG. 2 is a close-up photograph of the immature fruit.

FIG. 3 is a photograph of the fruit.

DETAILED DESCRIPTION OF THE PREFERRED EMBODIMENT

The color of the skin of the fruit is unique as shown in FIGS. 2 and 3. The shape of the fruit is oval. The fruit shape and color makes it very desirable. The average size is smaller, averaging 16 to 17 ozs. and is approximately 3½ to 4 inches in length and 2½ to 3 inches in width. The fruit is a bright golden color near 22B all over the oval shaped body except for a touch of light green at the stylar end. The flesh inside the fruit is orange in color near 25B, with very little fiber. The flesh is firm in texture and the taste is excellent. The seed size of the fruit is small in comparison to fruit size.

The color values expressed herein are those of The R.H.S. Colour Chart.

What is claimed is:

1. A new and distinct variety of tropical mango substantially as described and illustrated having a fruit characterized by a golden color with a light green blush at the stylar end on the surface of the fruit.

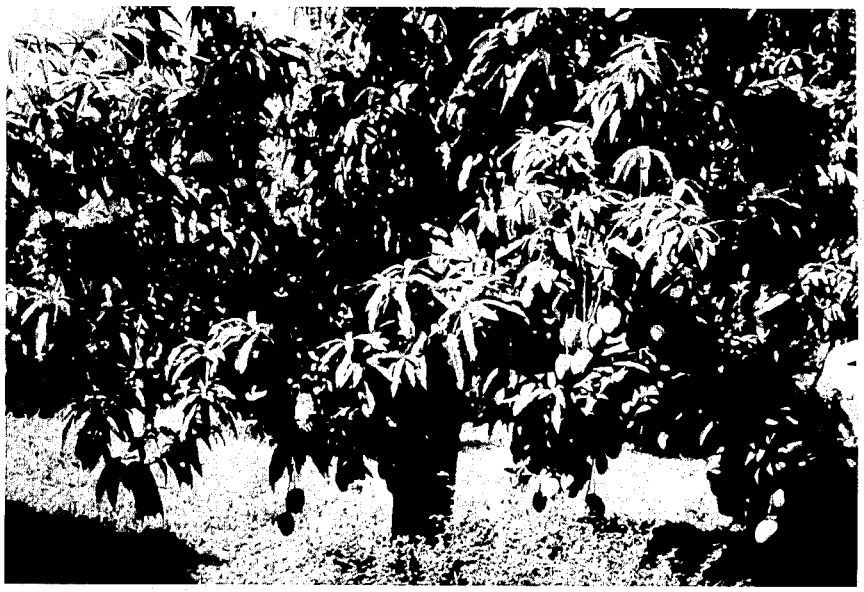
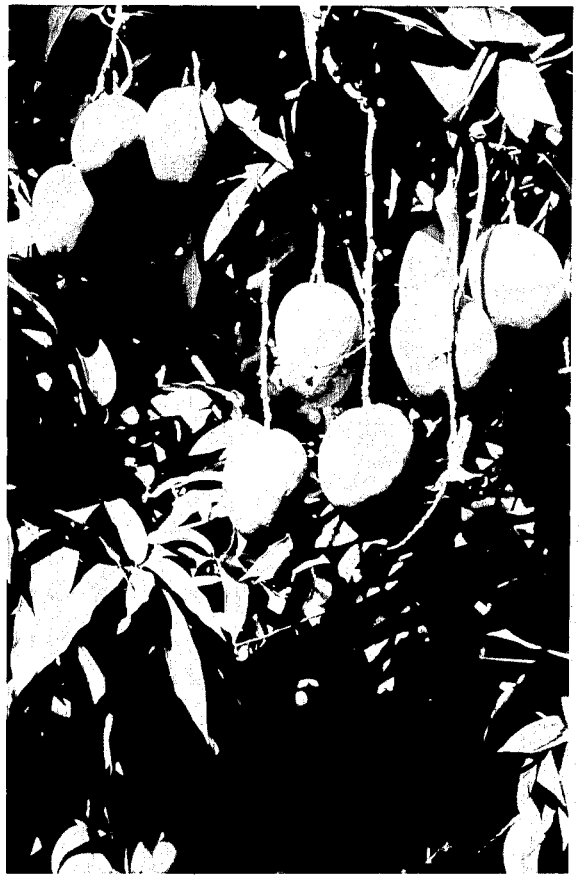

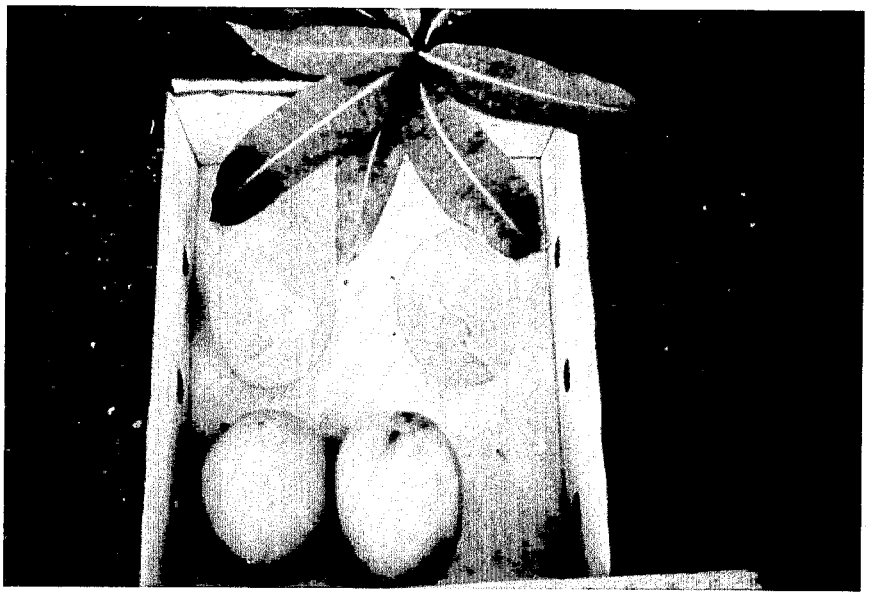

* * * * *